United States Patent
Xie et al.

(10) Patent No.: US 11,806,175 B2
(45) Date of Patent: Nov. 7, 2023

(54) FEW-VIEW CT IMAGE RECONSTRUCTION SYSTEM

(71) Applicants: Huidong Xie, Troy, NY (US); Ge Wang, Loudonville, NY (US); Hongming Shan, Troy, NY (US); Wenxiang Cong, Albany, NY (US)

(72) Inventors: Huidong Xie, Troy, NY (US); Ge Wang, Loudonville, NY (US); Hongming Shan, Troy, NY (US); Wenxiang Cong, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 47 days.

(21) Appl. No.: 17/642,725

(22) PCT Filed: Sep. 14, 2020

(86) PCT No.: PCT/US2020/050654
§ 371 (c)(1),
(2) Date: Mar. 14, 2022

(87) PCT Pub. No.: WO2021/051049
PCT Pub. Date: Mar. 18, 2021

(65) Prior Publication Data
US 2022/0375142 A1 Nov. 24, 2022

Related U.S. Application Data

(60) Provisional application No. 62/899,517, filed on Sep. 12, 2019, provisional application No. 63/077,745, filed on Sep. 14, 2020.

(51) Int. Cl.
*A61B 6/03* (2006.01)
*G06T 11/00* (2006.01)
*A61B 6/00* (2006.01)

(52) U.S. Cl.
CPC ............ *A61B 6/032* (2013.01); *A61B 6/5205* (2013.01); *G06T 11/005* (2013.01);
(Continued)

(58) Field of Classification Search
CPC ......... A61B 6/032; A61B 6/52; A61B 6/5205; A61B 6/5211; G06T 11/003;
(Continued)

(56) References Cited

U.S. PATENT DOCUMENTS 10,475,214 B2 * 11/2019 Fu ..................... G06T 11/003
10,709,394 B2 * 7/2020 Zhou ..................... A61B 6/032
(Continued)

FOREIGN PATENT DOCUMENTS

WO 2017223560 A1 12/2017
WO 2019147767 A1 8/2019

OTHER PUBLICATIONS

Huidong Xie, Hongming Shan, Wenxiang Cong, Xiaohua Zhang, Shaohua Liu, Ruola Ning, and Ge Wang, "Dual network architecture for few-view CT—trained on ImageNet data and transferred for medical imaging," Proc. SPIE 11113, Developments in X-Ray Tomography XII, 111130V (Sep. 10, 2019). (Year: 2019).*
(Continued)

*Primary Examiner* — Allen C. Ho
(74) *Attorney, Agent, or Firm* — Murtha Cullina LLP; Anthony P. Gangemi

(57) ABSTRACT

A system for few-view computed tomography (CT) image reconstruction is described. The system includes a preprocessing module, a first generator network, and a discriminator network. The preprocessing module is configured to apply a ramp filter to an input sinogram to yield a filtered sinogram. The first generator network is configured to receive the filtered sinogram, to learn a filtered back-projection operation and to provide a first reconstructed image as output. The first reconstructed image corresponds to the input sinogram. The discriminator network is configured to determine whether a received image corresponds to the first reconstructed image or a corresponding ground truth image. The generator network and the discriminator network correspond to a Wasserstein generative adversarial network (WGAN). The WGAN is optimized using an objective function based, at least in part, on a Wasserstein distance and based, at least in part, on a gradient penalty.

20 Claims, 4 Drawing Sheets

(52) U.S. Cl.
CPC ....... *G06T 11/006* (2013.01); *G06T 2211/421* (2013.01); *G06T 2211/436* (2013.01)

(58) Field of Classification Search
CPC ................ G06T 11/005; G06T 11/006; G06T 2211/421; G06T 2211/436
USPC .............................. 378/4, 210, 901; 382/131
See application file for complete search history.

(56) References Cited

U.S. PATENT DOCUMENTS

| | | | | |
|---|---|---|---|---|
| 10,832,392 | B2* | 11/2020 | Ceccaldi | G06N 3/047 |
| 10,970,887 | B2* | 4/2021 | Wang | A61B 5/00 |
| 10,984,565 | B2* | 4/2021 | Xing | G06N 3/084 |
| 11,049,223 | B2* | 6/2021 | Yang | A61B 6/12 |
| 11,076,824 | B1* | 8/2021 | Wang | G06N 3/044 |
| 11,257,259 | B2* | 2/2022 | Teixeira | A61B 5/055 |
| 11,410,374 | B2* | 8/2022 | Teixeira | A61B 5/1079 |
| 11,501,473 | B2* | 11/2022 | Zhang | G06T 11/005 |
| 11,514,621 | B2* | 11/2022 | Hu | G06T 11/006 |
| 11,580,410 | B2* | 2/2023 | Wang | G06T 11/006 |
| 11,593,977 | B2* | 2/2023 | Zhang | G06T 5/002 |
| 11,620,527 | B2* | 4/2023 | Murez | G06N 3/045 |
| | | | | 382/156 |
| 2019/0206095 | A1 | 7/2019 | Xing et al. | |
| 2019/0216409 | A1 | 7/2019 | Zhou et al. | |
| 2019/0244107 | A1 | 8/2019 | Murez et al. | |

OTHER PUBLICATIONS

International Search Report and The Written Opinion of the International Searching Authority, International Application No. PCT/US2020/050654, dated Dec. 7, 2020.

Xie, H., et al., "Dual Network Architecture for Few-view CT—Trained on ImageNet Data and Transferred for Medical Imaging," DeepAI.com, Ver. 1, Jul. 2, 2019.

* cited by examiner

FEW-VIEW CT IMAGE RECONSTRUCTION SYSTEM

CROSS REFERENCE TO RELATED APPLICATION(S)

This application claims the benefit of U.S. Provisional Application No. 62/899,517, filed Sep. 12, 2019, and U.S. Provisional Application No. 63/077,745, filed Sep. 14, 2020, which are incorporated by reference as if disclosed herein in their entirety.

GOVERNMENT LICENSE RIGHTS

This invention was made with government support under award numbers CA233888 and CA237267, awarded by the National Institutes of Health (NIH), and under award number EB026646, awarded by the National Institutes of Health (NIH). The government has certain rights in the invention.

FIELD

The present disclosure relates to few-view CT (computed tomography) image reconstruction.

BACKGROUND

X-ray computed tomography (CT) is a popular medical imaging method for screening, diagnosis, and image guided intervention. Although CT brings overwhelming healthcare benefits to patients, it may potentially increase cancer risk due to the involved ionizing radiation. Low-dose CT and few-view CT result in a reduced exposure to the ionizing radiation but typically at a cost of reduced image quality.

SUMMARY

In an embodiment, there is provided a system for few-view computed tomography (CT) image reconstruction. The system includes a preprocessing module, a first generator network, and a discriminator network. The preprocessing module is configured to apply a ramp filter to an input sinogram to yield a filtered sinogram. The first generator network is configured to receive the filtered sinogram, to learn a filtered back-projection operation and to provide a first reconstructed image as output. The first reconstructed image corresponds to the input sinogram. The discriminator network is configured to determine whether a received image corresponds to the first reconstructed image or a corresponding ground truth image. The first generator network and the discriminator network correspond to a Wasserstein generative adversarial network (WGAN). The WGAN is optimized using an objective function based, at least in part, on a Wasserstein distance and based, at least in part, on a gradient penalty.

In some embodiments, the system further includes a second generator network. The second generator network is configured to receive a concatenation of the first reconstructed image and a filtered back-projection of the input sinogram. The second generator network is further configured to provide a second reconstructed image. The discriminator network is further configured to determine whether the received image corresponds to the second reconstructed image.

In some embodiments of the system, the first generator network is configured to learn the filtered back-projection operation in a point-wise manner.

In some embodiments of the system, the first generator network includes a filtration portion, a back-projection portion, and a refinement portion.

In some embodiments of the system, the WGAN is trained, initially, using image data from an image database including a plurality of images.

In some embodiments of the system, the first generator network is configured to reconstruct the first reconstructed image using $O(C \times N \times N_v)$ parameters, where N is a dimension of the first reconstructed image, $N_v$ is a number of projections and C is an adjustable hyper-parameter in the range of 1 to N.

In some embodiments of the system, the second generator network corresponds to a refinement portion.

In an embodiment, there is provided a method for few-view computed tomography (CT) image reconstruction. The method includes applying, by a preprocessing module, a ramp filter to an input sinogram to yield a filtered sinogram; receiving, by a first generator network, the filtered sinogram; learning, by the first generator network, a filtered back-projection operation; and providing, by the first generator network, a first reconstructed image as output. The first reconstructed image corresponds to the input sinogram. The method further includes determining, by a discriminator network, whether a received image corresponds to the first reconstructed image or a corresponding ground truth image. The first generator network and the discriminator network correspond to a Wasserstein generative adversarial network (WGAN). The WGAN is optimized using an objective function based, at least in part, on a Wasserstein distance and based, at least in part, on a gradient penalty.

In some embodiments, the method further includes receiving, by a second generator network, a concatenation of the first reconstructed image and a filtered back-projection of the input sinogram; providing, by the second generator network, a second reconstructed image; and determining, by the discriminator network, whether the received image corresponds to the second reconstructed image.

In some embodiments of the method, the first generator network is configured to learn the filtered back-projection operation in a point-wise manner.

In some embodiments of the method, the first generator network includes a filtration portion, a back-projection portion, and a refinement portion.

In some embodiments, the method further includes learning, by the first generator network, an initial filtered back-projection operation using image data from an image database including a plurality of images.

In some embodiments of the method, the first generator network is configured to reconstruct the first reconstructed image using $O(C \times N \times N_v)$ parameters, where N is a dimension of the first reconstructed image, $N_v$ is a number of projections and C is an adjustable hyper-parameter in the range of 1 to N.

In some embodiments, the method further includes receiving, by a filtered back projection module, the input sinogram and providing, by the filtered back projection module, the filtered back-projection of the input sinogram.

In an embodiment, there is provided a computer readable storage device. The device has stored thereon instructions configured for few-view computed tomography (CT) image reconstruction. The instructions that when executed by one or more processors result in the following operations including: applying a ramp filter to an input sinogram to yield a filtered sinogram; receiving the filtered sinogram; learning a filtered back-projection operation; providing a first reconstructed image as output, the first reconstructed image corresponding to the input sinogram; and determining whether a received image corresponds to the first reconstructed image or a corresponding ground truth image, the operations corresponding to a Wasserstein generative adversarial network (WGAN). The WGAN is optimized using an objective function based, at least in part, on a Wasserstein distance and based, at least in part, on a gradient penalty.

In some embodiments of the device, the operations further include receiving a concatenation of the first reconstructed image and a filtered back-projection of the input sinogram; providing a second reconstructed image; and determining whether the received image corresponds to the second reconstructed image.

In some embodiments of the device, the filtered back-projection operation is learned in a point-wise manner.

In some embodiments of the device, the operations further include learning an initial filtered back-projection operation using image data from an image database including a plurality of images.

In some embodiments of the device, the first reconstructed image is reconstructed using $O(C \times N \times N_v)$ parameters, where N is a dimension of the first reconstructed image, $N_v$ is a number of projections and C is an adjustable hyper-parameter in the range of 1 to N.

BRIEF DESCRIPTION OF THE DRAWINGS

The drawings show embodiments of the disclosed subject matter for the purpose of illustrating features and advantages of the disclosed subject matter. However, it should be understood that the present application is not limited to the precise arrangements and instrumentalities shown in the drawings, wherein.

DETAILED DESCRIPTION

Figure 1:
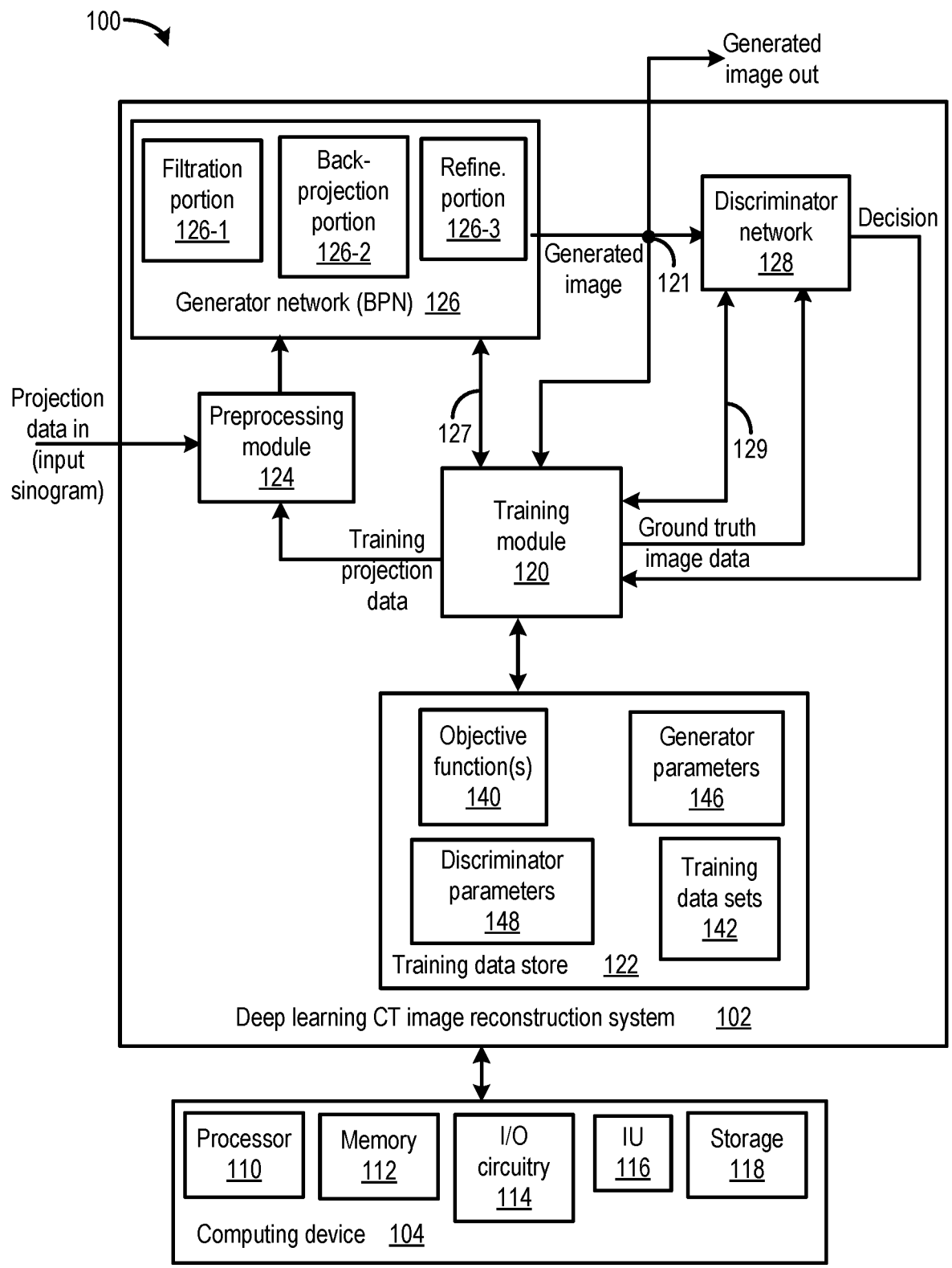
FIG. 1 illustrates a functional block diagram of a system that includes a deep learning CT image reconstruction system consistent with several embodiments of the present disclosure.

Current commercial CT scanners typically use one or two x-ray sources that are mounted on a rotating gantry to take hundreds of projections at different angles around a patient's body. The rotating mechanism is massive and consumes substantial energy related to a net angular momentum generated during the rotation. Thus, outside major hospitals, current commercial CT scanners are largely inaccessible due to their size, weight and expense. Few-view CT may be implemented in a mechanically stationary scanner thus avoiding the rotating mechanism and associated power consumption.

The Nyquist sampling theorem provides a lower bound on an amount of data used for image reconstruction. For example, when sufficient (i.e., above the Nyquist limit) projection data are acquired, analytic methods such as filtered back-projection (FBP) may provide relatively high quality CT image reconstruction. In few-view CT, due in part to under-sampled data, streak artifacts may be introduced in analytically reconstructed images because of incomplete projection data. Iterative techniques may incorporate prior knowledge in the image reconstruction but can be relatively time-consuming and may not produce satisfying results in some cases.

Generally, the present disclosure relates to a few-view CT image reconstruction system. In an embodiment, the few-view CT image reconstruction system corresponds to a deep efficient end-to-end reconstruction (DEER) network for few-view CT image reconstruction. In another embodiment, the few-view CT image reconstruction system corresponds to a dual network architecture (DNA) CT image reconstruction system. A method and/or system consistent with the present disclosure may be configured to receive CT scanner projection data (i.e., sinograms) and to generate a corresponding image. A system may include at least one generator network and a discriminator network configured as a generative adversarial neural network (GAN). The generator network(s) and the discriminator network correspond to artificial neural networks. In an embodiment, the generator network(s) and the discriminator network may correspond to convolutional neural networks. The generator network(s) and discriminator network may be trained, adversarially, as will be described in more detail below. The trained generator network(s) may then be configured to receive filtered few view projection data and to provide a reconstructed image as output.

In an embodiment, at least one generator network may correspond to a back projection network (BPN). The BPN may be configured to reconstruct a CT image directly from raw (i.e., sinogram) data using, for example, $O(C \times N \times N_v)$ parameters. N corresponds to dimension of reconstructed image and $N_v$ corresponds to number of projections. C is an adjustable hyper-parameter and is in the range of 1 to N. A BPN consistent with the present disclosure may thus be trainable on one consumer-level GPU (graphics processing unit). However, this disclosure is not limited in this regard. The BPN, similar to filtered back projection (FBP), is configured to learn a refined filtration back-projection process for reconstructing images directly from sinograms. For X-ray CT, each point in the sinogram domain relates to pixels/voxels on an X-ray path through a field of view. Thus, a plurality of line integrals acquired by a plurality of different detectors at particular angle are not related to each other. With this intuition, the reconstruction process of BPN is learned in a point-wise manner that facilitates constraining a memory burden.

In some embodiments, the generator network may be pre-trained using natural images from a publicly available image database, e.g., ImageNet. The generator network may then be refined using actual patient data. Advantageously, the complexity of natural images may facilitate learning the back-projection process.

FIG. 1 illustrates a functional block diagram of a system 100 that includes a deep learning CT image reconstruction system 102, consistent with several embodiments of the present disclosure. CT image reconstruction system 102 includes elements configured to implement training of a back projection network (BPN), as will be described in more detail below. System 100 further includes a computing device 104. Computing device 104 is configured to perform the operations of deep learning CT image reconstruction system 102.

The computing device 104 may include, but is not limited to, a server, a workstation computer, a desktop computer, a laptop computer, a tablet computer, an ultraportable computer, an ultramobile computer, a netbook computer and/or a subnotebook computer, etc. Computing device 104 includes a processor 110, a memory 112, input/output (I/O) circuitry 114, a user interface (UI) 116, and storage 118.

CT image reconstruction system 102 includes a training module 120, a training data store 122, a preprocessing module 124, a generator network 126, and a discriminator network 128. Generator network 126 includes a filtration portion 126-1, a back-projection portion 126-2 and a refinement portion 126-3. Generator network 126, after training, corresponds to a BPN. As used herein, the terms "generator network" and "generative network" are used interchangeably.

Processor 110 may include one or more processing units and is configured to perform operations of system 100, e.g., operations of training module 120, preprocessing module 124, generator network 126, and discriminator network 128. Memory 112 may be configured to store data associated with training module 120, preprocessing module 124, generator network 126, and discriminator network 128, and/or training data store 122. I/O circuitry 114 may be configured to communicate wired and/or wirelessly with a source of projection data and/or a recipient of a corresponding generated image. UI 116 may include a user input device (e.g., keyboard, mouse, microphone, touch sensitive display, etc.) and/or a user output device, e.g., a display. Storage 118 is configured to store at least a portion of training data store 122. Training data store 122 is configured to store training data including, but not limited to, one or more objective functions 140, one or more training data sets 142, generator parameters 146 and discriminator parameters 148.

Training module 120 is configured to manage training operations of generator network 126 (and discriminator network 128). Training module 120 may thus be configured to provide training projection data to preprocessing module 124 and ground truth image data to discriminator network 128. The training projection data and ground truth image data may be stored, for example, in training data store 122 as training data sets 142. Training module 120 may be further configured to provide an objective function, e.g., objective function 140, to discriminator network 128 and to receive a decision from discriminator network. Training module 120 may be further configured to provide, adjust and/or receive generator parameters 127 and/or discriminator parameters 129 during training operations. Such parameters may include, for example, neural network weights. Generator parameters may be stored in training data store as generator parameters 146 and discriminator parameters may be stored in training data store as discriminator parameters 148. After training, i.e., during normal operations, the generator parameters may be set, CT image reconstruction system 102 may be configured to receive projection data in (corresponding to an actual CT sinogram) and may be configured to provide a corresponding generated image 121 as generated image output.

CT image reconstruction may be expressed as:

$$I_{FV} = R^{-1}(S_{SV}) \quad (1)$$

where $I_{FV} \in \mathbb{R}^{w \times w}$ is an object image with dimension w×w, $S_{SV} \in \mathbb{R}^{v \times w}$ is the sinogram with dimension v×w and $R^{-1}$ corresponds to an inverse radon transform (e.g., filtered back projection (FBP)) in an instance where sufficient two dimensional (2D) projection data is available. When sufficient 2D projection data is available, CT image reconstruction can be reduced to solving a system of linear equations. If the number of linear equations is less than the number of unknown pixels as in the few-view CT setting, the image reconstruction is an underdetermined problem. Deep learning (DL) may be utilized to extract features of raw data for image reconstruction. With a deep neural network, as described herein, training data corresponds to prior knowledge configured to establish a relationship between a sinogram and the corresponding CT image. Thus, a trained deep neural network may be configured to efficiently solving this undetermined problem.

In operation, CT image reconstruction system 102 is configured as a Wasserstein Generative Adversarial Network (WGAN) to optimize (i.e., train) generator network 126. After optimization, generator network 126 may correspond to a back projection network (BPN). The BPN 126 is configured to receive preprocessed, as described herein, few view CT projection data, and to reconstruct a corresponding CT image.

A WGAN generally includes a generator network, e.g., generator network 126, and a discriminator network, e.g., discriminator network 128. The generator network 126 aims at reconstructing images directly from a batch of few-view sinograms. The discriminator network 128 is configured to receive generated image data 121 from generator network 126 or ground truth image data from, e.g., training module 120, and intends to distinguish whether an image is real (i.e., ground truth) or fake (from generator network 126). Both networks 126, 128 are configured to be optimized during the training process. If an optimized discriminator network 128 can hardly distinguish fake images from real images, then generator network 126 can fool discriminator network 128 which is the goal of WGAN. In other words, if discriminator network 128 is unable to distinguish between a generated image from the generator network 126 and a ground truth image, the generator network 126 has been optimized, i.e., is trained. The discriminator network 128 may facilitate improving a texture of the final image and reduce occurrence of over-smoothing.

WGAN is configured to replace a cross-entropy loss function of a non-Wasserstein generative adversarial network (GAN) with the Wasserstein distance. The Wasserstein distance is configured to improve the training stability during the training process compared to the GAN. In an embodiment, an objective function used during training includes the Wasserstein distance as well as a gradient penalty term. The objective function of the discriminator network 128 may be written as:

$$\min_{\theta_G} \max_{\theta_D} \{ \mathbb{E}_{S_{SV}}[D(G(S_{SV}))] - \mathbb{E}_{I_{FV}}[D(I_{FV})] + \lambda \mathbb{E}_{\tilde{I}}[(\|\nabla(\tilde{I})\|_2 - 1)^2] \} \quad (2A)$$

where D corresponds to operation of the discriminator network 128, G corresponds to operation of the generator network 126, $S_{SV}$ and $I_{FV}$ represent sparse-view sinograms and ground-truth images, respectively. Terms of the form $\mathbb{E}_a[b]$ in Eq. 2A denote an expectation of b as a function of a. $\theta_G$ and $\theta_D$ represent the trainable parameters of the generator network 126 and the discriminator network 128, respectively. $\tilde{I} = \alpha \cdot I_{FV} + (1-\alpha) \cdot G(S_{SV})$. $\alpha$ is uniformly sampled from the interval [0,1]. In other words, $\tilde{I}$ represents images between fake and real images. $\nabla(\tilde{I})$ denotes the gradient of D with respect to $\tilde{I}$. $\lambda$ is a parameter used to balance the Wasserstein distance term and gradient penalty term. The generator network 126 and the discriminator network 128 (e.g., the generator parameters and the discriminator parameters) may be updated iteratively.

The input to the BPN 126 is a batch of few-view sinograms. According to Fourier slice theorem, low-frequency information is sampled denser than high-frequency information. It may be appreciated that performing back-projection directly on the batch of few-view sinograms may result in blurry reconstructed images. Preprocessing module 124 is configured to implement a ramp filter to filter received projection data (i.e., sinogram) to avoid this blurry issue. The ramp filter operation may be performed on sinograms in the Fourier domain as multiplication. The filter length may be set as twice the length of the sinogram. Theoretically, the length of the filter is infinitely long for a bandlimited signal, but it is not practical in reality. Since values of the filter outside twice the length of sinograms are generally at or near zero, filter length is set as twice the length of sinograms. The filtered sinograms, i.e., output of the preprocessing module 124, may then be provided to the generator network 126.

Generator network 126 is configured to learn a revised filtration back-projection operation and output reconstructed images, i.e., generated image 121. Generator network 126 includes three components: a filtration portion 126-1, a back-projection portion 126-2 and a refinement portion 126-3.

In filtration portion 126-1, a plurality of one dimensional (1-D) convolutional layers are used to learn small variance to filtered sinograms. Because the filtration portion 126-1 is a multi-layer CNN, different layers can learn different parts of the filter. In one nonlimiting example, the 1-D convolutional window may be set as one quarter the length of the sinograms. The length of the 1-D convolutional window is configured to reduce computational burden. The idea of residual connection may be used to preserve high-resolution information and prevent gradient from vanishing. Inspired by the ResNeXt structure, in one nonlimiting example, a cardinality of the convolutional layers may be 3. It may be appreciated that increasing the cardinality of the network may be more effective than increasing the depth or width of the network when the network capacity is increased. In BPN 126, the value of the cardinality may correspond to a number of branches.

The learned sinograms from the filtration portion 126-1 may then be provided to the back-projection portion 126-2. It may be appreciated that each point in the sinogram relates to pixel values on the x-ray path through corresponding object image and any other pixels do not contribute to the point. Thus, the reconstruction process may be learned in a point-wise manner using a point-wise fully-connected layer. Thus, the generator network 126, by learning in a point-wise manner, may learn the back-projection process with relatively fewer parameters compared to other methods. Learning with relatively fewer parameters may utilize relatively fewer memory resources. In other words, for a sinogram with dimension $N_v \times N$, there is a total of $N_v \times N$ relatively small fully-connected layers in the method, as described herein. The respective input to each of these relatively small fully-connected layers is a single point in the sinogram and the output is a line with dimension $N \times 1$. After this point-wise fully-connected layer, rotation and summation may be applied to simulate FBP, and to put all the learned lines to their appropriate positions. Bilinear interpolation may be used for rotating images and maintaining the rotated image on a Cartesian grid.

This network design is configured to allow the corresponding neural network to learn the reconstruction process using N parameters. In some situations, due to the relative complexity of medical images and incomplete projection data (due to the few-view input data), N parameters may not be sufficient for learning relatively high-quality images. Thus, in an embodiment, the number of parameters may be increased to $O(C \times N \times N_v)$ in this point-wise fully-connected layer to by increasing the number of branches to C (an adjustable hyper-parameter). The increase in number of parameters is further supported by using a different set of parameters for different angles in order to compensate the negative effect introduced by bilinear interpolation. An amount of bias terms in this point-wise fully-connected layer is the same as the amount of weights in order to learn fine details in medical images. Bias terms are added along the detector direction. Then, there is one 2-D convolutional layer with 3×3 kernel and stride 1 configured to combine all the learned mappings from sinogram domain to image domain. It should be noted that by learning in this point-wise manner, each point in the sinogram becomes a training sample instead of a whole sinogram and in order to reduce training time, a plurality of fully-connected layers may be implemented together by one piece-wise multiplication.

Images reconstructed in the back-projection portion 126-2 may then be provided to the last portion of generator network 126, i.e., the refinement portion 126-3. Refinement portion 126-3 may be configured to remove remaining artifacts. For example, the refinement portion 126-3 may correspond to a U-net, including conveying paths, and may be built with ResNeXt structure. The conveying paths are configured to copy early feature maps and reuse them as part of the input to later layers. Concatenation is used to combine early and later feature maps along the channel dimension. The generator network 126 may then be configured to preserve high-resolution features. Each layer in the U-net may be followed by a rectified linear unit (ReLU). 3×3 kernels may be used in both convolutional and transpose-convolutional layers. A stride of 2 may be used for down-sampling and up-sampling layers and stride of 1 may be used for all other layers. In order to maintain the tensor's size, zero-padding is used.

The discriminator network 128 is configured to receive input from either generator network 126 (i.e., generated image 121) or the ground-truth dataset (e.g., ground truth image data from training module 120). As described herein, the discriminator network 128 may be configured to distinguish whether the input is real or fake. In one nonlimiting example, the discriminator network 128 may contain 6 convolutional layers with 64, 64, 128, 128, 256, 256 filters, respectively, and followed by 2 fully-connected layers with number of neurons 1024 and 1, respectively. A leaky ReLU activation function may be used after each layer with a slope of 0.2, for example, in the negative part. A convolutional window of 3×3 and zero-padding may be used for all convolutional layers. Stride may be equal to 1 for odd layers and 2 for even layers.

Generally, the objective function used for optimizing a generator network may include one or more of mean square error (MSE), adversarial loss and structural similarity index (SSIM). MSE may effectively suppress back-ground noise, but may result in over-smoothed images. Generally, MSE may not be sensitive to image texture. MSE generally assumes background noise is white Gaussian noise that is independent of local image features. The formula of MSE loss may be expressed as:

$$L_2 = \frac{1}{N_b \cdot W \cdot H} \sum_{i=1}^{N_b} \|Y_i - X_i\|_2^2 \qquad (3)$$

where $N_b$, W and H correspond to the number of batches, image width and image height respectively. $Y_i$ and $X_i$ represent ground-truth image and image reconstructed by generator network 126, respectively. In order to compensate the disadvantages of MSE and acquire visually better images, SSIM is introduced in the objective function. SSIM aims to measure structural similarity between two images. In one nonlimiting example, the convolution window used to measure SSIM is set as 11×11. The SSIM formula is expressed as:

$$SSIM(Y, X) = \frac{(2\mu_Y\mu_X + C_1)(2\sigma_{YX} + C_2)}{(\mu_Y^2 + \mu_X^2 + C_1)(\sigma_Y^2 + \sigma_X^2 + C_2)} \quad (4)$$

where $C_1=(K_1 \cdot R)^2$ and $C_2=(K_2 \cdot R)^2$ are constants used to stabilize the formula if the denominator is small. R stands for the dynamic range of pixel values and, in one nonlimiting example, $K_1=0.01$ and $K_2=0.03$. $\mu_Y$, $\mu_X$, $\sigma_Y^2$, $\sigma_X^2$, and $\sigma_{YX}$ are the means of Y and X, variances of Y and X and the covariance between Y and X, respectively. The structural loss may then be expressed as:

$$L_{sl}=1-SSIM(Y,X) \quad (5)$$

The adversarial learning technique used in BPN aims to help generator network 126 produce sharp images that are indistinguishable by the discriminator network 128. Referring to Eq. 1, adversarial loss may be written as:

$$L_{al}=-\mathbb{R}_{S_{SV}}[D(G(S_{SV}))] \quad (6)$$

The overall objective function of the generator network 126 may then be written as:

$$L_G=\lambda_Q \cdot L_{al}+\lambda_P \cdot L_{sl}+L_2 \quad (7A)$$

where $\lambda_Q$ and $\lambda_P$ are hyper-parameters used to balance different loss functions.

Thus, a deep efficient end-to-end reconstruction (DEER) network for few-view CT image reconstruction system, consistent with the present disclosure, may include a generator network and a discriminator network. The generator network and discriminator network may be trained, adversarially, using a WGAN framework, as described herein. The DEER network for few-view CT image reconstruction system may then be configured to receive CT scanner projection data (i.e., sinograms), to filter the received projection data and to generate a corresponding image. In some embodiments, the generator network and discriminator network may be pre-trained using, for example, ImageNet data. The CT image reconstruction process of the BPN network is learned in a point-wise manner that facilitates constraining a memory burden.

Figure 2:
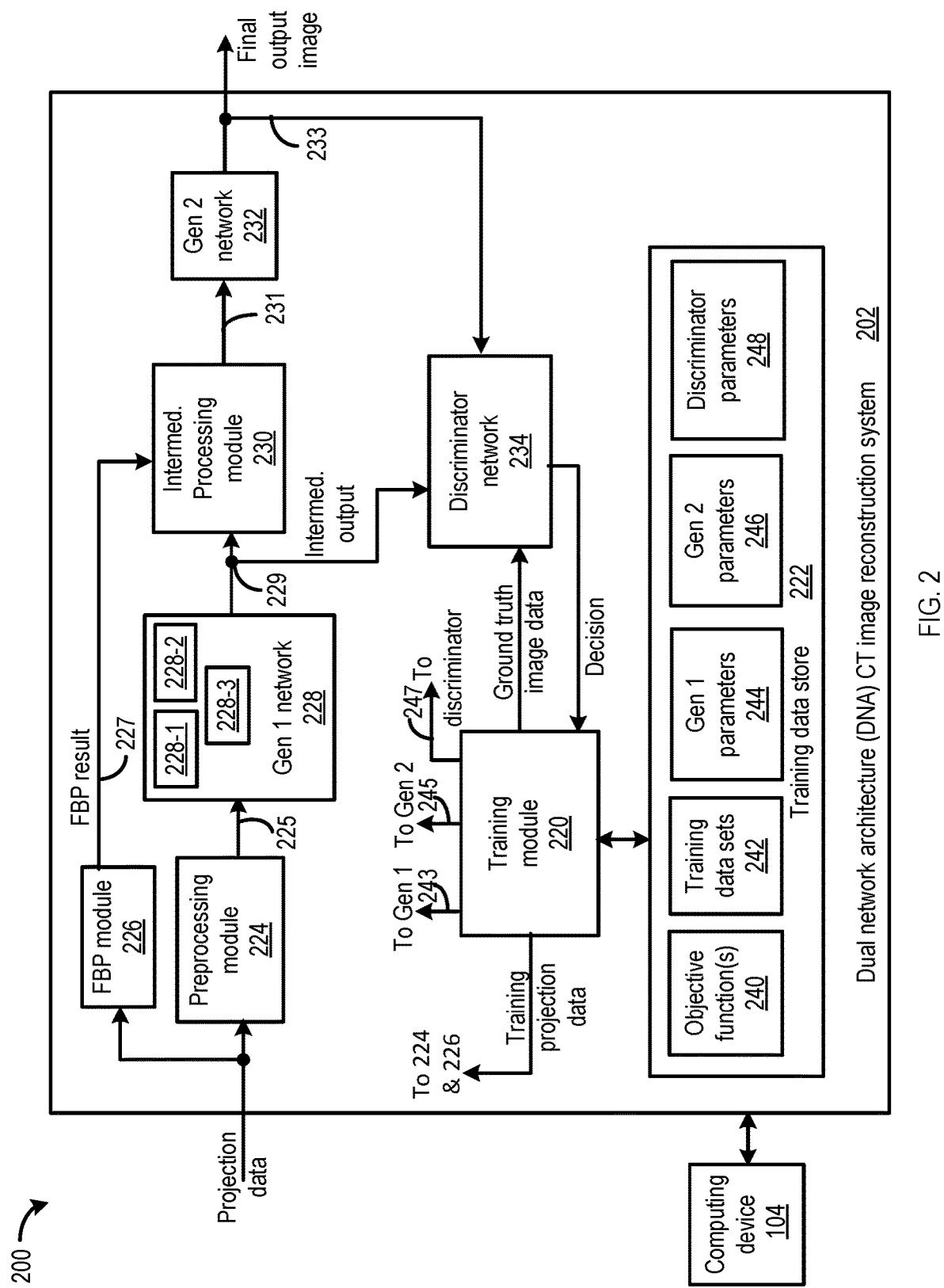
FIG. 2 illustrates a functional block diagram of a system that includes a dual network architecture (DNA) CT image reconstruction system consistent with several embodiments of the present disclosure.

FIG. 2 illustrates a functional block diagram of system 200 that includes a dual network architecture (DNA) CT image reconstruction system 202 consistent with several embodiments of the present disclosure. DNA system 202 includes elements configured to implement training generator network(s) and a discriminator network, as will be described in more detail below. System 200 further includes computing device 104, as described herein. Computing device 104 is configured to perform the operations of dual network CT image reconstruction system 202. Storage 118 may be configured to store at least a portion of training data store 222, as described herein.

It may be appreciated that DNA CT image reconstruction system 202 has at least some elements and features in common with CT image reconstruction system 102 of FIG. 1. In the interest of descriptive efficiency, the common elements and features will be only briefly described, with reference provided to the description herein related to the CT image reconstruction system 102 of FIG. 1.

CT image reconstruction system 202 includes a training module 220, a training data store 222, a preprocessing module 224, a filtered back projection (FBP) module 226, a first generator network (Gen 1) 228, an intermediate processing module 230, a second generator network (Gen 2) 232, and a discriminator network 234. Training data store 222 is configured to store training data including, but not limited to, one or more objective function(s) 240, one or more training data sets 242, first generator (Gen 1) parameters 244, second generator (Gen 2) parameters 246, and discriminator parameters 248.

The preprocessing module 224 corresponds to preprocessing module 124 of FIG. 1. The first generator (Gen 1) network 228 corresponds to the generator network 126 of FIG. 1. Similar to the deep learning CT image reconstruction system 102 of FIG. 1, DNA CT image reconstruction system 202 is configured to receive CT scanner projection data (i.e., sinograms) and to generate (i.e., reconstruct) a corresponding image (Final output image 233). The DNA CT image reconstruction system 202 may be trained, adversarially, as described herein. A subsystem that includes preprocessing module 224, trained generator networks 228, 232 and intermediate processing module 230, may then be configured to receive filtered projection data and to provide a reconstructed image as output.

DNA CT image reconstruction system 202 includes two generator networks: Gen 1 network 228 and Gen 2 network 232. As used herein, the terms "G1", "Gen 1" and "Gen 1 network" are used interchangeably and all refer to Gen 1 network 228 of FIG. 2. As used herein, the terms "G2", "Gen 2" and "Gen 2 network" are used interchangeably and all refer to Gen 2 network 232 of FIG. 2. Training module 220 is configured to manage training operations of generator networks 228 and 232 and discriminator network 234, similar to training module 120.

Training module 220 may thus be configured to provide training projection data (i.e., input sinogram) to preprocessing module 224 and FBP module 226. Training module 220 may be further configured to provide ground truth image data to discriminator network 234. The training projection data and ground truth image data may be stored, for example, in training data store 222 as training data sets 242. Training module 220 may be further configured to provide an objective function, e.g., objective function 240, to discriminator network 234 and to receive a decision from discriminator network. Training module 220 may be further configured to provide, adjust and/or receive Gen 1 parameters 243, Gen 2 parameters 245, and/or discriminator parameters 247 during training operations. Such parameters may include, for example, neural network weights. Gen 1 parameters may be stored in training data store as Gen 1 parameters 244, Gen 2 parameters may be stored in training data store as Gen 2 parameters 246, and discriminator parameters may be stored in training data store as discriminator parameters 248. After training, i.e., during normal operations, the Gen 1 and Gen 2 parameters may be set, CT image reconstruction system 202 may be configured to receive projection data in (corresponding to an actual CT sinogram) and may be configured to provide a corresponding generated image as final output image 233.

In operation, preprocessing module 224 and FBP module 226 are configured to receive training projection data (e.g., a batch of few-view sinograms) from, e.g., training module 220. Preprocessing module 224 is configured to filter the few-view sinograms to yield filtered few view sinograms 225. In one nonlimiting example, the filter length may be twice the length of the sinogram. The filtering corresponds to a ramp filter applied to the sinograms in the Fourier domain, as described herein.

The filtered few-view sinograms 225 may then be provided to Gen 1 network 228. Gen 1 network 228 corresponds to generator network 126 of FIG. 1. Gen 1 network 228 is configured to operate on the filtered few-view sinograms (i.e., to learn a filtered back projection technique) to produce an intermediate output 229. The intermediate output 229 may correspond to reconstructed image that may then be provided to the intermediate processing module 230. The FBP module 226 is configured to perform filtered back-projection on the received training projection data (e.g., a batch of few-view sinograms) and to provide an FBP result 227 to the intermediate processing module 230. The intermediate processing module 230 is configured to concatenate the intermediate output 229 with the FBP result 227 and to provide the concatenated result 231 to the Gen 2 network 232. The Gen 2 network 232 is configured to operate on the concatenated result 231 (e.g., to optimize the concatenated result) to produce a final output image 233. The intermediate output 229 and the final output image 233 may be further provided to the discriminator network 234. The discriminator network 234 is further configured to receive ground truth image data and to provide at least one decision indicator to, for example, training module 220.

Similar to generator network 126 of FIG. 1, the Gen 1 network 228 may include three portions: filtration 228-1, back-projection 228-2, and refinement 228-3. The filtration portion 228-1 may correspond to a multi-layer CNN. In the filtration part 228-1, 1-D convolutional layers are used to produce filtered data. In one nonlimiting example, filter length of filtration portion 228-1 may be set to twice a length of a projection vector. It may be appreciated that the length of the projection vector may be shortened. Since the filtration is done through a multi-layer CNN, different layers can learn different parts of the filter. In one nonlimiting example, the 1-D convolutional window may be empirically set as one quarter the length of the projection vector to reduce the computational burden. Residual connections may be used to preserve high-resolution information and to prevent gradient from vanishing.

The learned sinogram from the filtration portion 228-1 may then be provided to the back-projection portion 228-2. The back-projection portion 228-2 is configured to perform back-projection operations on the received learned sinogram. Operation of the back-projection portion 228-2 is inspired by the following intuition: every point in the filtered projection vector only relates to pixel values on the x-ray path through the corresponding object image and any other data points in this vector contribute nothing to the pixels on this x-ray path. As is known a single fully-connected layer can be implemented to learn the mapping from the sinogram domain to the image domain, but relies on relatively large matrix multiplications in this layer that may tax memory. To reduce the memory burden, DNA CT image reconstruction system 202 (e.g., Gen 1 network 228) is configured to learn the reconstruction process in a point-wise manner using a point-wise fully-connected layer. Back-projection portion 228-2 may then learn the back-projection process. The input to the point-wise fully-connected layer corresponds to a single point in the filtered projection vector. The number of neurons may then correspond to a width of the corresponding image. After this point-wise fully-connected layer, rotation and summation operations are applied to simulate the analytical FBP method. Bilinear interpolation may be used for rotating images. In one nonlimiting example, C may be empirically set as 23, allowing the network to learn multiple mappings from the sinogram domain to the image domain. The value of C can be understood as the number of branches. Different view-angle may use different parameters. Although the proposed filtration and back-projection parts all together learn a refined FBP method, streak artifacts may not be eliminated perfectly. An image reconstructed by the back-projection part 228-2 may thus be provided to the refinement portion 228-3 of Gen 1 for refinement.

The refinement portion 228-1 may correspond to a U-net with conveying paths and may be constructed with the ResNeXt structure. In one nonlimiting example, U-net may be configured to contain 4 down-sampling and 4 up-sampling layers. Each layer may have a stride of 2 and may be followed by a rectified linear unit (ReLU). A 3×3 kernel may be included in both convolutional and transpose-convolutional layers. The number of kernels in each layer is 36. To maintain the tensors size, zero-padding is used.

Gen 2 network 232 is configured to have a same structure as the refinement portion 228-3 in Gen 1. The input 231 to G2 is a concatenation of FBP-result 227 and output 229 from G1. With the use of G2, the network becomes deep. As a result, the benefits of deep learning can be utilized in this direct mapping for CT image reconstruction.

In operation, similar to the deep learning CT image reconstruction system 102 of FIG. 1, DNA CT image reconstruction system 202 is optimized using the Wasserstein Generative Adversarial Network (WGAN) framework. As described herein, the DNA CT image reconstruction system 202 includes three components: two generator networks: Gen 1 network 228 and Gen 2 network 232, and a discriminator network 234. Gen 1 and Gen 2 aim at reconstructing images directly from a batch of few-view sinograms. The discriminator network 234 is configured to receive images from Gen 1 and Gen 2 and a ground-truth dataset, and intends to distinguish whether an image is real (i.e., is from the ground-truth dataset) or fake (i.e., is from G1 or G2). The networks are configured to be optimized in the training process. If an optimized network D can hardly distinguish fake images from real images, then it is concluded that generators G1 and G2 can fool discriminator D which is the goal of GAN. The network D is configured to help to improve the texture of the final image and prevent over-smoothed issue from occurring.

Different from generative adversarial network (GAN), Wasserstein GAN (WGAN) replaces the cross-entropy loss function with the Wasserstein distance, improving the training stability during the training process, as described herein. In an embodiment, an objective function used during training of the DNA CT image reconstruction system 202 includes the Wasserstein distance as well as a gradient penalty term. The objective function of the WGAN framework for the DNA CT image reconstruction system 202 may be expressed as:

$$\min_{\theta_{G_1},\theta_{G_2}} \max_{\theta_D} \{\mathbb{E}_{S_{SV}}[D(G_1(S_{SV}))] - \mathbb{E}_{I_{FV}}[D(I_{FV})] - \qquad (2B)$$

$$[D(G_2(I_{SV}))] - \mathbb{E}_{I_{FV}}[D(I_{FV})] + \lambda \mathbb{E}_{\hat{I}}[(\|\nabla(\hat{I})\|_2 - 1)^2]\}$$

where $S_{SV}$, $I_{SV}=G_f(S_{SV})$, $I_{FV}$ represent a sparse-view sinogram, an image reconstructed by Gen 1 from a sparse-view sinogram and the ground-truth image reconstructed from the full-view projection data, respectively. Similar to Eq. 2A, terms of the form $\mathbb{R}_a[b]$ in Eq. 2B denote an expectation of b as a function of a. $\theta_{G_1}$, $\theta_{G_2}$ and $\theta_D$ represent the trainable parameters of Gen 1 network 228, Gen 2 network 232 and Discriminator network 234, respectively. $\bar{I}$ represents images between fake (from G1 or G2) and real (from the ground-truth dataset) images. $\nabla(\bar{I})$ denotes the gradient of D with respect to $\bar{I}$. The parameter $\lambda$ balances the Wasserstein distance terms and gradient penalty terms. G1, G2 and D may be updated iteratively.

The objective function for optimizing the generator networks, Gen 1 and Gen 2, may include the mean square error (MSE), structural similarity index (SSIM) and adversarial loss. MSE is a popular choice for denoising applications, which effectively suppresses the background noise but could result in over-smoothed images. Generally, MSE may be insensitive to image texture since it assumes background noise is white Gaussian noise and is independent of local image features. The formula of MSE loss ($L_2$) is expressed as Eq. 3, as described herein, where $N_b$, W and H denote the number of batches, image width and image height respectively. $Y_i$ and $X_i$ represent ground-truth image and image reconstructed by generator networks (G1 or G2), respectively.

To compensate for the disadvantages of MSE and acquire visually better images, SSIM is introduced in the objective function. The SSIM formula may be expressed as Eq. 4, as described herein. The structural loss may then be expressed as Eq. 5, as described herein.

The adversarial loss aims to assist the generators 228, 232, producing sharp images that are indistinguishable by the discriminator network 234. Referring to Eq. 2B, adversarial loss for Gen 1 may be expressed as:

$$L_{al}^{(1)} = -\mathbb{R}_{S_{SV}}[D(G_1(S_{SV}))] \quad (6A)$$

and adversarial loss for G2 is expressed as:

$$L_{al}^{(2)} = -\mathbb{R}_{S_{SV}}[D(G_2(I_{SV}))] \quad (6B)$$

It may be appreciated that solving the few-view CT image reconstruction is similar to solving a set of linear equations when the number of equations is not sufficient to perfectly resolve all the unknowns. DNA CT image reconstruction system 202 is configured to estimate the unknown by combining the information from the existing equations and the knowledge contained in the big data. MSE between the original sinogram and the synthesized sinogram from a reconstructed image (from Gen 1 or Gen 2) may be included as part of the objective function, which may be written as:

$$L_2^{sino} = \frac{1}{N_b \cdot V \cdot H} \sum_{i=1}^{N_b} \|Y_i^{sino} - X_i^{sino}\|_2^2 \quad (3B)$$

where $N_b$, V, H denote the number of batches, number of views and sinogram height, respectively. $Y_i^{sino}$ represents the original sinogram and $X_i^{sino}$ represents sinogram from a reconstructed image (from Gen 1 or Gen 2).

Both generator networks, Gen 1, Gen 2 may be updated at the same time. The overall objective function of two generators, e.g., generator networks 228, 232, may then be written as:

$$\min_{\theta_{G_1}, \theta_{G_2}} \quad (7B)$$

$$[\lambda_Q \cdot (L_{al}^{(1)} + L_{al}^{(2)}) + \lambda_P \cdot (L_{sl}^{(1)} + L_{sl}^{(2)}) + \lambda_R \cdot (L_2^{sino(1)} + L_2^{sino(2)}) + L_2^{(2)} + L_2^{(1)}]$$

where the superscripts (1) and (2) indicate that the term is for measurements between ground-truth images and results reconstructed by G1 and G2, respectively. $\lambda_Q$, $\lambda_P$ and $\lambda_R$ are hyper-parameters used to balance different loss functions.

The discriminator network 234 is configured to receive inputs from G1 and G2, and the ground-truth dataset, and to try to distinguish whether each input is real or fake. In one nonlimiting example, the discriminator network 234 may include 6 convolutional layers with 64, 64, 128, 128, 256, 256 filters and followed by 2 fully-connected layers with numbers of neurons 1,024 and 1, respectively. The leaky ReLU activation function may be used after each layer with a slope of 0.2, for example, in the negative part. A 3×3 kernel and zero-padding are used for all the convolutional layers, with stride equal 1 for odd layers and stride equal 2 for even layers.

Thus, a dual network architecture CT image reconstruction system, consistent with the present disclosure, may include a plurality of generator networks and a discriminator network. The generator networks and discriminator network may be trained, adversarially, using a WGAN framework, as described herein. The DNA CT image reconstruction system may then be configured to receive CT scanner projection data (i.e., sinograms), to filter the received projection data and to generate a corresponding image. The CT image reconstruction process of the generator networks is learned in a point-wise manner that facilitates constraining a memory burden. In some embodiments, the generator network(s) and discriminator network may be pre-trained using, for example, ImageNet data.

Figure 3:
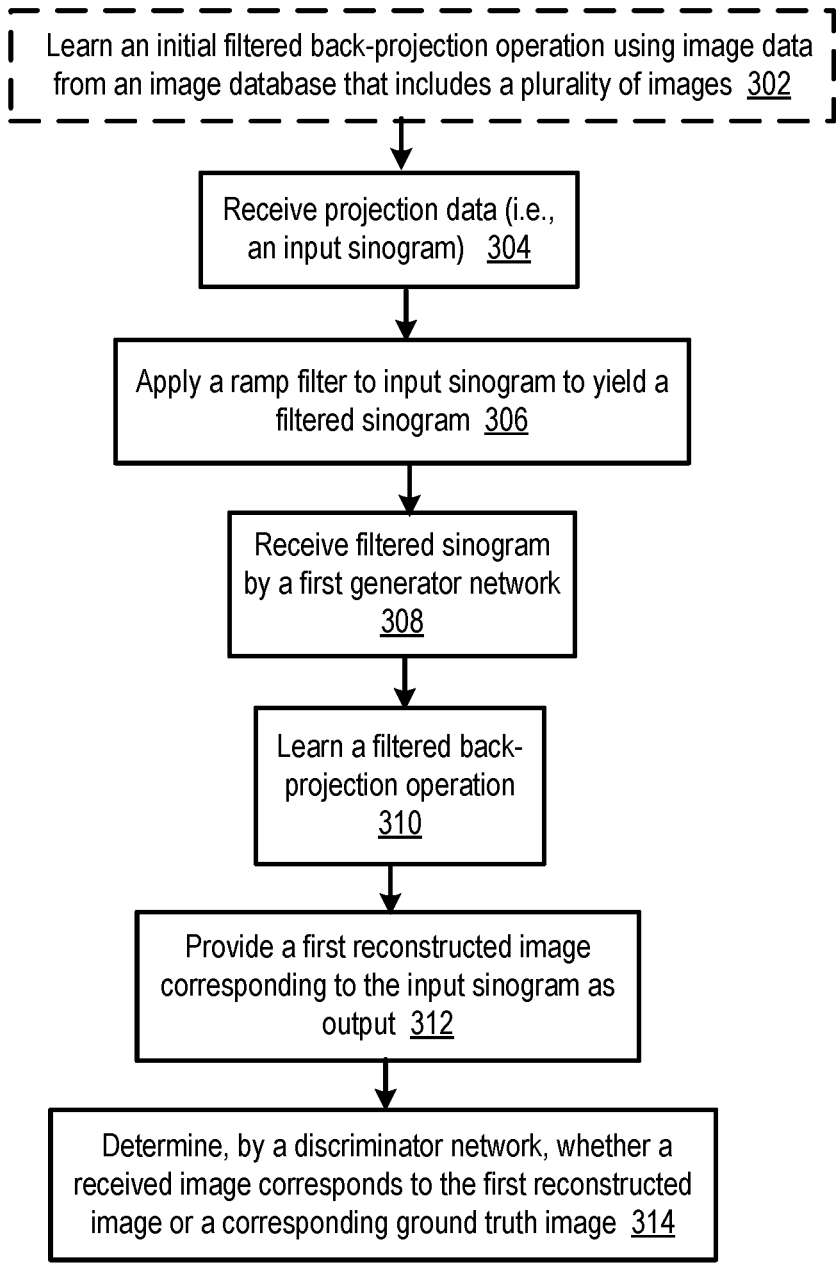
FIG. 3 is a flow chart of deep learning CT image reconstruction system training operations according to various embodiments of the present disclosure.

FIG. 3 is a flowchart 300 of deep learning CT image reconstruction training operations according to various embodiments of the present disclosure. In particular, the flowchart 300 illustrates training a deep learning CT image reconstruction system to reconstruct an image from a few-view sinogram. The operations may be performed, for example, by deep learning CT image reconstruction system 102 (e.g., preprocessing module 124, generator network 126, and/or discriminator network 128) of FIG. 1.

In some embodiments, operations may include operation 302. Operation 302 includes learning an initial filtered back-projection operation using image data from an image database that includes a plurality of images. For example, the image database may correspond to ImageNet. Operation 304 may include receiving projection data (i.e., an input sinogram). A ramp filter may be applied to the input sinogram to yield a filtered sinogram at operation 306. The filtered sinogram may be received by a first generator network at operation 308. Operation 310 may include learning a filtered back-projection operation. A first reconstructed image corresponding to the input sinogram may be provided as output at operation 312. Operation 314 may include determining, by a discriminator network, whether a received image corresponds to the first reconstructed image or a corresponding ground truth image. The generator network and the discriminator network correspond to a Wasserstein generative adversarial network (WGAN). The WGAN is optimized using an objective function based, at least in part, on a Wasserstein distance and based, at least in part, on a gradient penalty.

Thus, a deep learning CT image reconstruction system may be trained for few-view CT image reconstruction.

Figure 4:
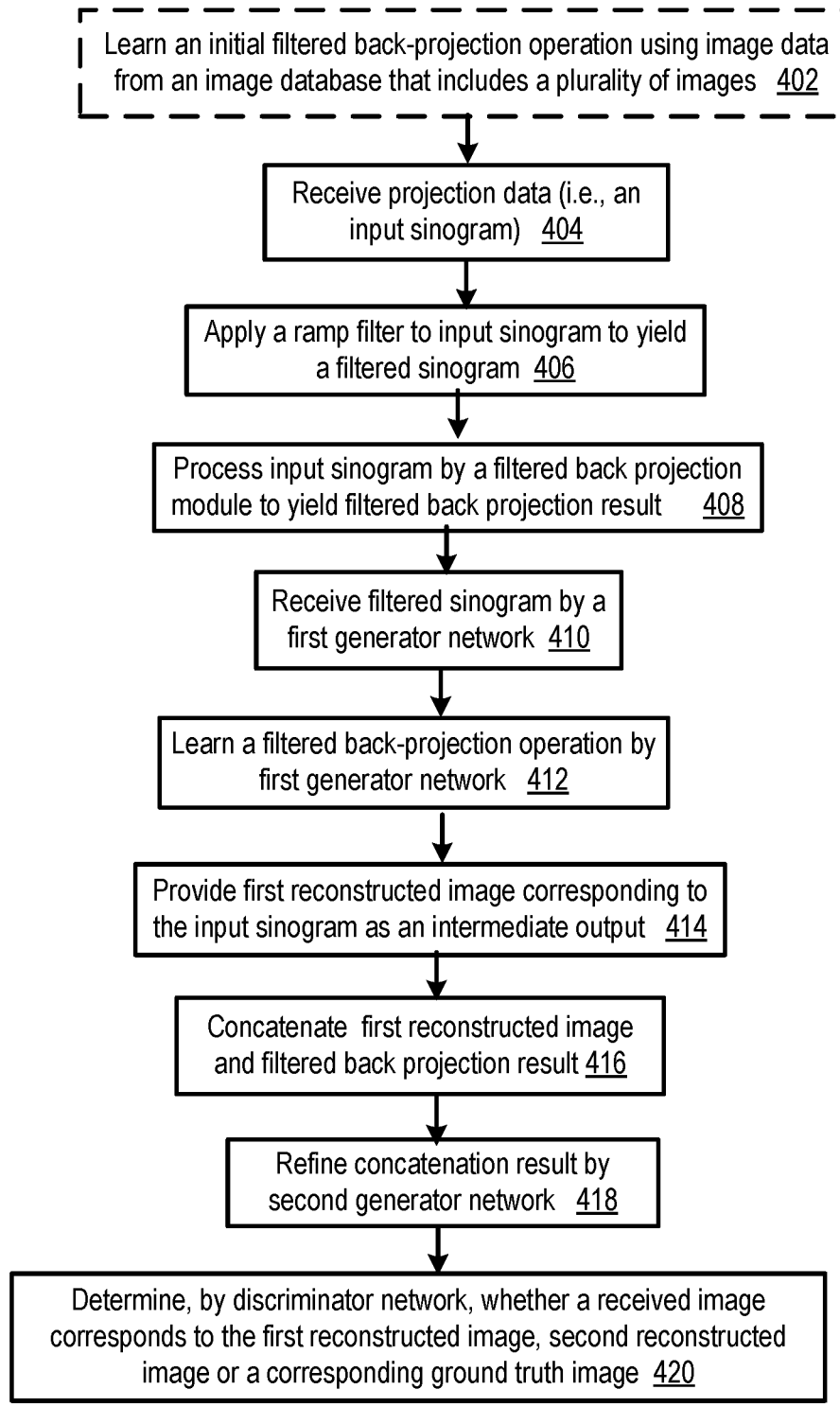
FIG. 4 is a flow chart of dual network architecture (DNA) CT image reconstruction system training operations according to various embodiments of the present disclosure.

FIG. 4 is a flow chart 400 of dual network architecture (DNA) CT image reconstruction system training operations according to various embodiments of the present disclosure. In particular, the flowchart 400 illustrates training a DNA CT image reconstruction system to reconstruct an image from a few-view sinogram. The operations may be performed, for example, by DNA CT image reconstruction system 202 (e.g., preprocessing module 224, filtered back projection (FBP) module 226, first generator network (Gen 1) 228, intermediate processing module 230, second generator network (Gen 2) 232, and/or discriminator network 234) of FIG. 2.

In some embodiments, operations may include operation 402. Operation 402 includes learning an initial filtered back-projection operation using image data from an image database that includes a plurality of images. For example, the image database may correspond to ImageNet. Operation 404 may include receiving projection data (i.e., an input sinogram). A ramp filter may be applied to an input sinogram to yield a filtered sinogram at operation 406. The input sinogram may be processed by a filtered back projection module to yield a filtered back projection result at operation 408. The filtered sinogram may be received by a first generator network at operation 410. Operation 412 may include learning a filtered back-projection operation by the first generator network. A first reconstructed image corresponding to the input sinogram may be provided as an intermediate output at operation 414. The first reconstructed image and a filtered back projection result may be concatenated at operation 416. Operation 418 may include refining a concatenation result by a second generator network. Operation 420 may include determining, by a discriminator network, whether a received image corresponds to the first reconstructed image, the second reconstructed image or a corresponding ground truth image. The generator networks and the discriminator network correspond to a Wasserstein generative adversarial network (WGAN). The WGAN is optimized using an objective function based, at least in part, on a Wasserstein distance and based, at least in part, on a gradient penalty.

Thus, a DNA CT image reconstruction system may be trained for few-view CT image reconstruction.

As used in any embodiment herein, the terms "logic" and/or "module" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may include, for example, singly or in any combination, hard-wired circuitry, programmable circuitry such as computer processors comprising one or more individual instruction processing cores, state machine circuitry, and/or firmware that stores instructions executed by programmable circuitry. The logic and/or module may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc.

The foregoing provides example system architectures and methodologies, however, modifications to the present disclosure are possible. The processor 110 may include one or more processing units and may be configured to perform operations of one or more circuitries, modules and/or artificial neural networks. Processing units may include, but are not limited to, general-purpose processing units, graphical processing units, parallel processing units, etc.

Memory 112 may include one or more of the following types of memory: semiconductor firmware memory, programmable memory, non-volatile memory, read only memory, electrically programmable memory, random access memory, flash memory, magnetic disk memory, and/or optical disk memory. Either additionally or alternatively system memory may include other and/or later-developed types of computer-readable memory.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A few-view computed tomography (CT) image reconstruction system, the system comprising:
    a preprocessing module configured to apply a ramp filter to an input sinogram to yield a filtered sinogram;
    a first generator network configured to receive the filtered sinogram, to learn a filtered back-projection operation and to provide a first reconstructed image as an output, the first reconstructed image corresponding to the input sinogram; and
    a discriminator network configured to determine whether a received image corresponds to the first reconstructed image or a corresponding ground truth image, the first generator network and the discriminator network corresponding to a Wasserstein generative adversarial network (WGAN), the WGAN optimized using an objective function based, at least in part, on a Wasserstein distance and based, at least in part, on a gradient penalty.

2. The system of claim 1, further comprising a second generator network configured to receive a concatenation of the first reconstructed image and a filtered back-projection of the input sinogram and to provide a second reconstructed image, the discriminator network further configured to determine whether the received image corresponds to the second reconstructed image.

3. The system of claim 2, wherein the second generator network corresponds to a refinement portion.

4. The system of claim 2, further comprising a filtered back projection module configured to receive the input sinogram and to provide the filtered back-projection of the input sinogram.

5. The system of claim 1, wherein the first generator network is configured to learn the filtered back-projection operation in a point-wise manner.

6. The system of claim 1, wherein the first generator network comprises a filtration portion, a back-projection portion, and a refinement portion.

7. The system of claim 1, wherein the WGAN is trained, initially, using image data from an image database comprising a plurality of images.

8. The system of claim 1, wherein the first generator network is configured to reconstruct the first reconstructed image using $O(C \times N \times N,)$ parameters, where N is a dimension of the first reconstructed image, N, is a number of projections, and C is an adjustable hyper-parameter in the range of 1 to N.

9. A method for few-view computed tomography (CT) image reconstruction, the method comprising:
applying, by a preprocessing module, a ramp filter to an input sinogram to yield a filtered sinogram;
receiving, by a first generator network, the filtered sinogram;
learning, by the first generator network, a filtered back-projection operation;
providing, by the first generator network, a first reconstructed image as an output, the first reconstructed image corresponding to the input sinogram; and
determining, by a discriminator network, whether a received image corresponds to the first reconstructed image or a corresponding ground truth image, the first generator network and the discriminator network corresponding to a Wasserstein generative adversarial network (WGAN), the WGAN optimized using an objective function based, at least in part, on a Wasserstein distance and based, at least in part, on a gradient penalty.

10. The method of claim 9, further comprising:
receiving, by a second generator network, a concatenation of the first reconstructed image and a filtered back-projection of the input sinogram;
providing, by the second generator network, a second reconstructed image; and
determining, by the discriminator network, whether the received image corresponds to the second reconstructed image.

11. The method of claim 10, further comprising receiving, by a filtered back projection module, the input sinogram and providing, by the filtered back projection module, the filtered back-projection of the input sinogram.

12. The method of claim 9, wherein the first generator network is configured to learn the filtered back-projection operation in a point-wise manner.

13. The method of claim 9, wherein the first generator network comprises a filtration portion, a back-projection portion, and a refinement portion.

14. The method of claim 9, further comprising learning, by the first generator network, an initial filtered back-projection operation using image data from an image database comprising a plurality of images.

15. The method of claim 9, wherein the first generator network is configured to reconstruct the first reconstructed image using $O(C \times N \times N,)$ parameters, where N is a dimension of the first reconstructed image, N, is a number of projections, and C is an adjustable hyper-parameter in the range of 1 to N.

16. A computer readable storage device having stored thereon instructions configured for a few-view computed tomography (CT) image reconstruction, the instructions that when executed by one or more processors result in the following operations comprising:
applying a ramp filter to an input sinogram to yield a filtered sinogram;
receiving the filtered sinogram;
learning a filtered back-projection operation;
providing a first reconstructed image as an output, the first reconstructed image corresponding to the input sinogram; and
determining whether a received image corresponds to the first reconstructed image or a corresponding ground truth image, the operations corresponding to a Wasserstein generative adversarial network (WGAN), the WGAN optimized using an objective function based, at least in part, on a Wasserstein distance and based, at least in part, on a gradient penalty.

17. The device of claim 16, wherein the instructions that when executed by the one or more processors result in the following additional operations comprising:
receiving a concatenation of the first reconstructed image and a filtered back-projection of the input sinogram;
providing a second reconstructed image; and
determining whether the received image corresponds to the second reconstructed image.

18. The device of claim 16, wherein the filtered back-projection operation is learned in a point-wise manner.

19. The device of claim 16, wherein the instructions that when executed by the one or more processors result in the following additional operations comprising learning an initial filtered back-projection operation using image data from an image database comprising a plurality of images.

20. The device of claim 16, wherein the first reconstructed image is reconstructed using $O(C \times N \times N,)$ parameters, where N is a dimension of the first reconstructed image, N, is a number of projections, and C is an adjustable hyper-parameter in the range of 1 to N.

* * * * *